United States Patent
Limb et al.

(10) Patent No.: US 8,691,207 B2
(45) Date of Patent: Apr. 8, 2014

(54) TRANSPLANTATION OF CELLS EXPRESSING MARKERS FOR PHOTORECEPTOR CELLS AND RETINAL GANGLION CELLS INDUCED FROM MÜLLER STEM CELLS

(75) Inventors: Gloria Astrid Limb, London (GB); Peng Tee Khaw, London (GB)

(73) Assignee: The Institute of Ophthalmology, London (GB)

( * ) Notice: Subject to any disclaimer, the term of this patent is extended or adjusted under 35 U.S.C. 154(b) by 0 days.

(21) Appl. No.: 13/341,042

(22) Filed: Dec. 30, 2011

(65) Prior Publication Data
US 2012/0100215 A1    Apr. 26, 2012

Related U.S. Application Data

(63) Continuation of application No. 10/580,770, filed as application No. PCT/GB2004/005101 on Dec. 3, 2004, now Pat. No. 8,173,426.

(30) Foreign Application Priority Data

Dec. 3, 2003 (GB) .................................. 0328021.1

(51) Int. Cl.
*A01K 63/00* (2006.01)
*A01K 65/00* (2006.01)

(52) U.S. Cl.
USPC .......................................... 424/93.1; 435/377

(58) Field of Classification Search
None
See application file for complete search history.

(56) References Cited

U.S. PATENT DOCUMENTS

| | | | |
|---|---|---|---|
| 6,183,735 B1 | 2/2001 | Greenwood et al. | |
| 6,298,270 B1 | 10/2001 | Nisch et al. | |
| 2002/0039788 A1 | 4/2002 | Isseroff et al. | |
| 2003/0207450 A1* | 11/2003 | Young et al. | 435/368 |
| 2004/0087016 A1 | 5/2004 | Keating et al. | |

FOREIGN PATENT DOCUMENTS

| | | |
|---|---|---|
| WO | WO 91/02499 A1 | 3/1991 |
| WO | WO 94/25569 A1 | 11/1994 |
| WO | WO 97/19694 A1 | 6/1997 |
| WO | WO 00/10580 A2 | 3/2000 |
| WO | WO 01/58460 A1 | 8/2001 |

OTHER PUBLICATIONS

Limb et al. Current Prospects for Adult Stem Cell—Based Therapies in Ocular Repair and Regeneration. Current Eye Res., 2006, vol. 31, pp. 381-390.*
Bhatia et al. Adult Retinal Stem Cells Revisited. Open Ophthalmology Jornal, 2010, vol. 4, pp. 30-38.*
Canola et al. Retinal Stem Cells Transplanted into Models of Late Stages of Retinitis Pigmentosa Preferentially Adopt a Glial or a Retinal Ganglion Cell Fate. Investigative Ophthalmology & Visual Sci., 2007, vol. 48, pp. 446-454.*
Khodair et al. Cyclic AMP Prevents Retraction of Axon Terminals in Photoreceptors Prepared for Transplantation: An In Vitro Study. Investigative Ophthalmology & Visual Sci., 2005, vol. 46, pp. 967-973.*
Ahmad, I. et al. "Identification of Neural Progenitors in the Adult Mammalian Eye" *Biochemical and Biophysical Research Communications*, 2000, 270(2):517-521.
Fischer, A.J. et al. "Identification of a Proliferating Marginal Zone of Retinal Progenitors in Postnatal Chickens" *Developmental Biology*, 2000, 220:197-210.
Fischer, A.J. et al. "Insulin and Fibroblast Growth Factor 2 Activate a Neurogenic Program in Müller Glia of the Chicken Retina" *The Journal of Neuroscience*, Nov. 1, 2002, 22(21):9387-9398.
Fischer, A.J. et al. "Potential of Müller Glia to Become Neurogenic Retinal Progenitor Cells" *GLIA*, 2003, 43:70-76.
Guidry, C. et al. "Tractional Force Generation by Human Müller Cells: Growth Factor Responsiveness and Integrin Receptor Involvement" *Investigative Ophthalmology & Visual Science*, Mar. 2003, 44(3):1355-1363.
Jaynes, C.D. et al. "Mücell survival and proliferation in response to medium conditioned by the retinal pigment epithelium" *Brain Research*, 1995, 678:55-64.
Kelley, M.W. et al. "Regulation of Proliferation and Photoreceptor Differentiation in Fetal Human Retinal Cell Cultures" *Investigative Ophthalmology & Visual Science*, Jun. 1995, 36(7):1280-1289.
Limb, G.A. et al. "In Vitro Characterization of a Spontaneously Immortalized Human Müller Cell Line.(MIO-M1)" *Investigative Ophthalmology and Visual Science*, Mar. 2002, 43(3):864-869.
Limb, G.A. et al. "Differential Expression of Matrix Metalloproteinases 2 and 9 by Glial Müller Cells: Response to Soluble and Extracellular Matrix-Bound Tumor Necrosis Factor-α" *American Journal of Pathology*, May 2002, 160(5):1847-1855.
Tropepe, V. et al. "Retinal Stem Cells in the Adult Mammalian Eye" *Science*, Mar. 17, 2000, 287:2032-2036.
Walcott, J.C. et al. "Müller cells express the neuronal progenitor cell marker nestin in both differentiated and undifferentiated human foetal retina" *Clinical and Experimental Ophthalmology*, 2003, 31:246-249.
Yang, P. et al. "In Vitro Isolation and Expansion of Human Retinal Progenitor Cells" *Experimental Neurology*, 2002, 177:326-331.

* cited by examiner

*Primary Examiner* — Deborah Crouch
(74) *Attorney, Agent, or Firm* — Saliwanchik, Lloyd & Eisenschenk

(57) ABSTRACT

A method for the production of retinal cells, useful in transplantation therapy, comprises: (i) obtaining one or more mammalian adult Müller cells; and (ii) culturing the cells in the presence of an extracellular matrix protein and a growth factor to thereby induce dedifferentiation of the Müller cells into a progenitor phenotype.

4 Claims, 8 Drawing Sheets

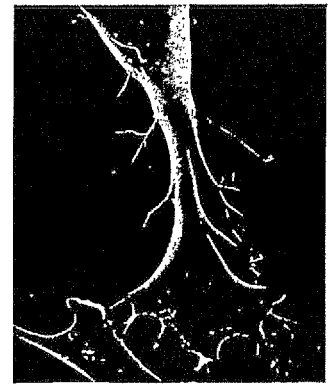
Figure 1

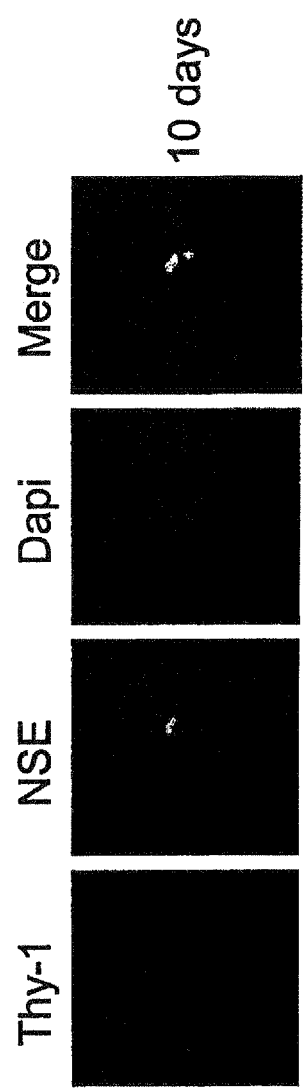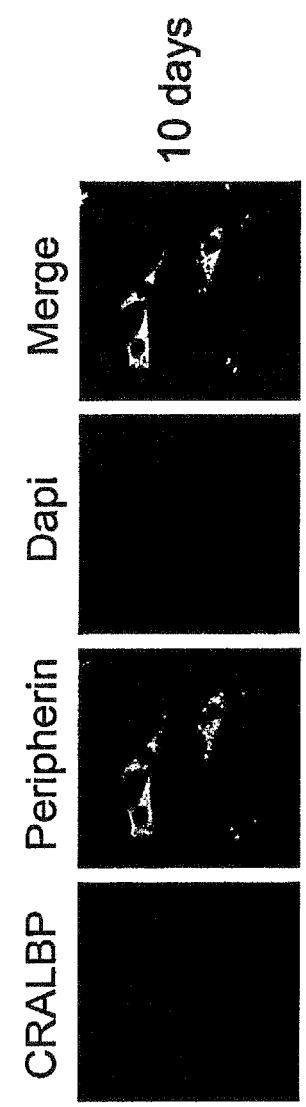
Figure 5

TRANSPLANTATION OF CELLS EXPRESSING MARKERS FOR PHOTORECEPTOR CELLS AND RETINAL GANGLION CELLS INDUCED FROM MÜLLER STEM CELLS

CROSS-REFERENCE TO RELATED APPLICATIONS

This application is a continuation of U.S. patent application Ser. No. 10/580,770, filed May 24, 2007, which is the national stage of PCT Application Number PCT/GB2004/005101, filed Dec. 3, 2004, the disclosure of each of which is incorporated herein by reference in its entirety, including all figures, tables, amino acid and nucleic acid sequences.

FIELD OF THE INVENTION

The present invention relates to the restoration of visual function by cell transplantation. In particular, the present invention relates to the use of adult Müller stem cells in the treatment of visual disorders, neurological disorders, repair of the peripheral nervous system and spinal cord repair.

BACKGROUND TO THE INVENTION

The restoration of visual function is one of the ultimate aims in vision research. Present treatments for severe diseases leading to blindness, such as age related macular degeneration (AMD), glaucoma, diabetic retinopathy and complications of retinal detachment, are only supportive or slow down disease progression, but do not restore visual function. Recent research involving stem cell transplantation in a wide disease spectrum has triggered enthusiasm across the medical and scientific community, and stem cell research to restore neural circuits in diseased retinas are encouraged by results obtained with progenitor cell transplantation to treat other human diseases, including leukemia, severe skin burns and myocardial disfunction.

To date, transplantation studies aimed at restoration of human retinal function have yielded little success, and have been limited to transplantation of retinal pigment epithelial (RPE) and Iris pigment epithelial (IPE) cells. Experimental transplantation of RPE, Schwann and brain-derived pre-cursor cells in animal models of retinal degeneration has provided some success in the preservation of retinal function. Retinal transplantation of brain-derived precursor cells to RCS rats (a model of retinal degeneration) promotes photoreceptor cell survival. However, although the transplanted cells migrate to the photoreceptor cell layer, they fail to express retinal neural markers, suggesting that a specific neuronal precursor is needed for functional and morphological regeneration of the retina.

During early studies, it was thought that stem cells could only be isolated from embryos, for which neural progenitors were first identified in the embryonic mammalian central system and peripheral nervous system (CNS and PNS).

However, more recent investigations have identified adult stem cells in
neurogenic regions of the CNS, and this has prompted further investigations in the search for adult stem cells.

Limb et al., IOVS, 2002; 43(3); 864-869 discloses the identification of a spontaneously immortalised Müller cells.

Müller cells are radial glial cells that extend vertically through the whole width of the retina. They stabilise the complex retinal architecture, give structural and metabolic support to neurons and blood vessels, prevent aberrant photoreceptor migration into the sub-retinal space and regulate fluid transport between the vitreous cavity and the sub-retinal space. Nearly all retinal pathological conditions that constitute major causes of blindness, including age related macular degeneration, proliferative diabetic retinopathy, proliferative vitreoretinopathy (PVR) and retinitis pigmentosa (RP), are associated with changes in Müller cell distribution, proliferation or function.

Fischer et al., Nature Neuroscience, 2001; 4(3): 247-252 describes the identification of Müller glial cells obtained from the retina of post-natal chicken. The Müller glial cells are shown to be non-differentiated, proliferate and express transcription factors normally expressed by embryonic retinal progenitors. The Müller glial cells proliferate in response to retinal damage.

In the human eye, it has been shown that Müller stem cells given origin to various retinal cells are found during foetal development, but no evidence has yet been shown that these cells may be present in the adult neural retina. There is therefore a need to develop cells suitable for use in retinal cell transplantation therapies, for the treatment of human retinal damage.

SUMMARY OF THE INVENTION

The present invention is based on the realisation that Müller cells from the adult human neural retina can be obtained and made to behave like stem cells under appropriate conditions.

According to a first aspect of the invention, a method for the production on retinal cells, useful in transplantation therapy, comprises steps of:

(i) obtaining one or more mammalian adult Müller cells; and (ii) culturing the cells in the presence of an extra-cellular matrix protein and a growth factor, to thereby induce the de-differentiation of the Müller cells into a progenitor phenotype.

The ability to take adult mammalian Müller cells and treat them to induce de-differentiation, allows large quantities of the cells to be obtained and used in transplantation therapy. The cells used according to the invention have been shown to preserve retinal integrity and attenuate loss of visual function when injected into the sub-retinal space of RCS rats.

According to a second aspect of the invention, retinal cells obtainable according to the method outlined above, are used in the manufacture of a medicament for the treatment of a condition associated with cell loss or cell damage in a mammalian eye.

According to a third aspect of the invention, a composition comprises cells obtained using the method defined above.

According to a fourth aspect of the invention, a composition comprises a matrix protein and one or more growth factors, in the manufacture of a medicament for administration to a damaged eye, to repair the damage.

According to a fifth aspect of the invention, a structure for grafting to a patient comprises multiple layers of a matrix supporting material onto which is incorporated a plurality of retinal neurons, the retinal neurons of one layer being of the same or different phenotype to those of other layers.

DESCRIPTION OF THE DRAWINGS

The invention is described with reference to the accompanying drawings, wherein:

FIG. 1 is a photographic representation of Müller cells, either (A) in plastic tissue culture dishes, (B) on plastic tissue culture dishes showing characteristic microvilli and (C) showing end foot processes;

FIG. 5 is a photographic representation of the expression of neural retinal markers by Müller cells cultured on matrigel in the presence of FGF2 and IGF-1;

DESCRIPTION OF THE INVENTION

The present invention allows for the identification, expansion and maintenance of adult human Müller progenitor cells, permitting the use of the cells in transplantation therapy, to treat various retinal disorders. The adult Müller cells may be isolated from a mammalian donor retina and express markers of mature cells, but on treatment in specific conditions in vitro, the cells re-enter the cell cycle and de-differentiate into cells expressing progenitor cell phenotypes such as nestin, sonic hedgehog protein, the transcription factors Sox-2, Pax-6 and Chx10 βIII tubulin and bind peanut agglutinin. They also express markers of differentiated retinal neurons, including HuD, cairetinin, calbindin, Brn 5.0, neuron-specific enolase, Thy-1, peripherin, rhodopsin and 70 kDa neurofilament protein.

The term "de-differentiation" is well known to those skilled in the art and refers to the change in a cell phenotype from a differentiated state to a progenitor phenotype.

Adult mammalian Müller cells may be obtained from the retina of an adult mammalian eye using techniques disclosed herein. It is preferable to isolate human Müller cells. Under normal culture conditions, the adult Müller cells will express markers of mature Müller cells, including cellular retinaldehyde binding protein (CRALBP), glutamine synthetase, vimentin and epidermal growth factor receptor (EGF-R) (Lewis et al., Exp. Eye Res., 1988; 47: 855-868). The Müller cells are identified by their characteristic morphology under phase-contrast microscopy and by their expression of the markers indicated above (Sarthy et al., Invest. Ophthalmol. Vis. Sci., 1998; 39: 212-216). When subconfluent, Müller cells in culture exhibit morphological characteristics typically observed in the retina in vivo: they are non-pigmented cells with elongated shape, characteristic end foot processes and villus surfaces (see FIGS. 1a, b and c); they respond to glutamate as judged by their electrophysiological responses, and do not express GFAP under non-stressed conditions.

Figure 2:
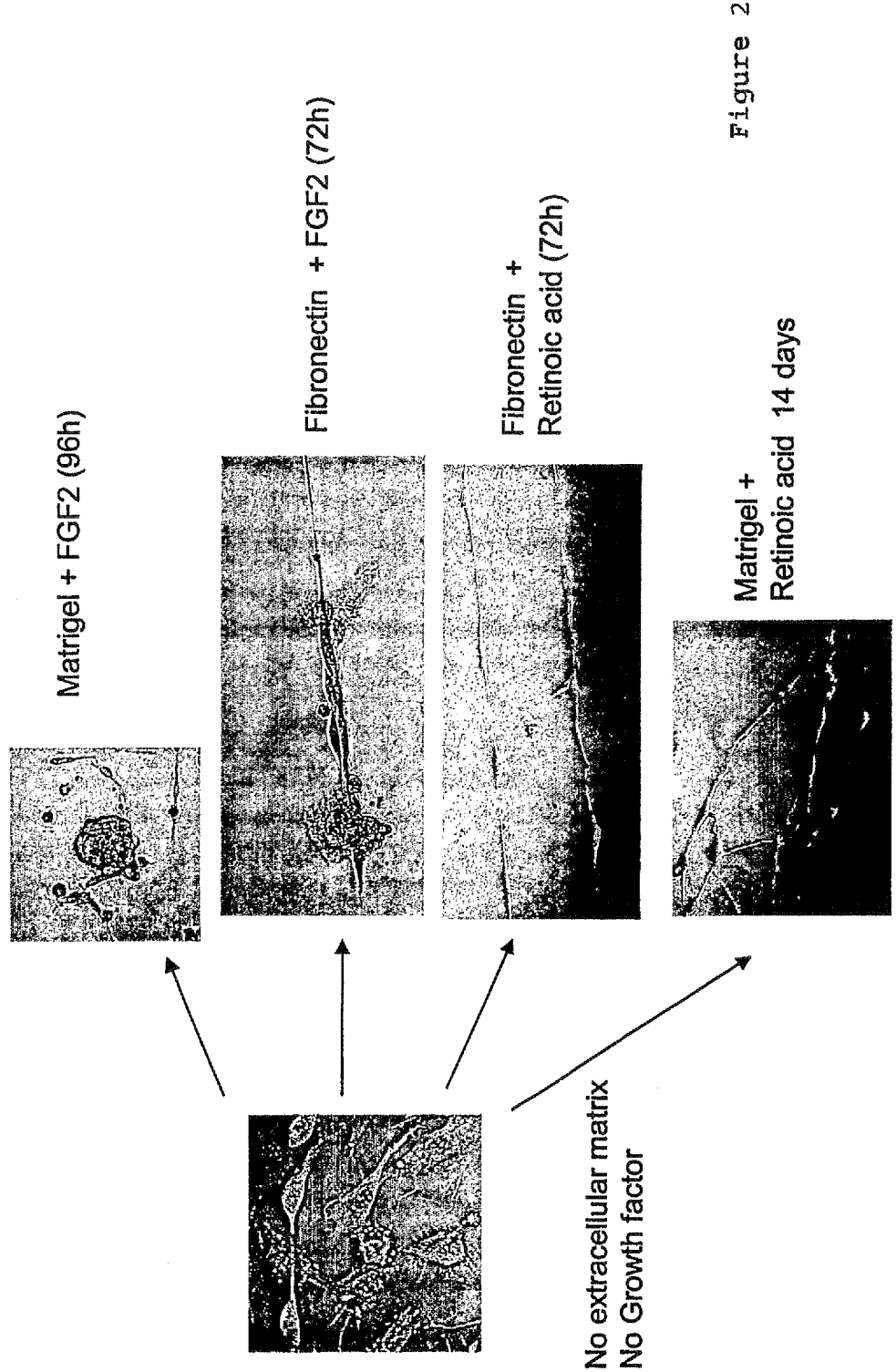
FIG. 2 is a photographic representation of Müller cells grown under different culture conditions.
Figure 3:
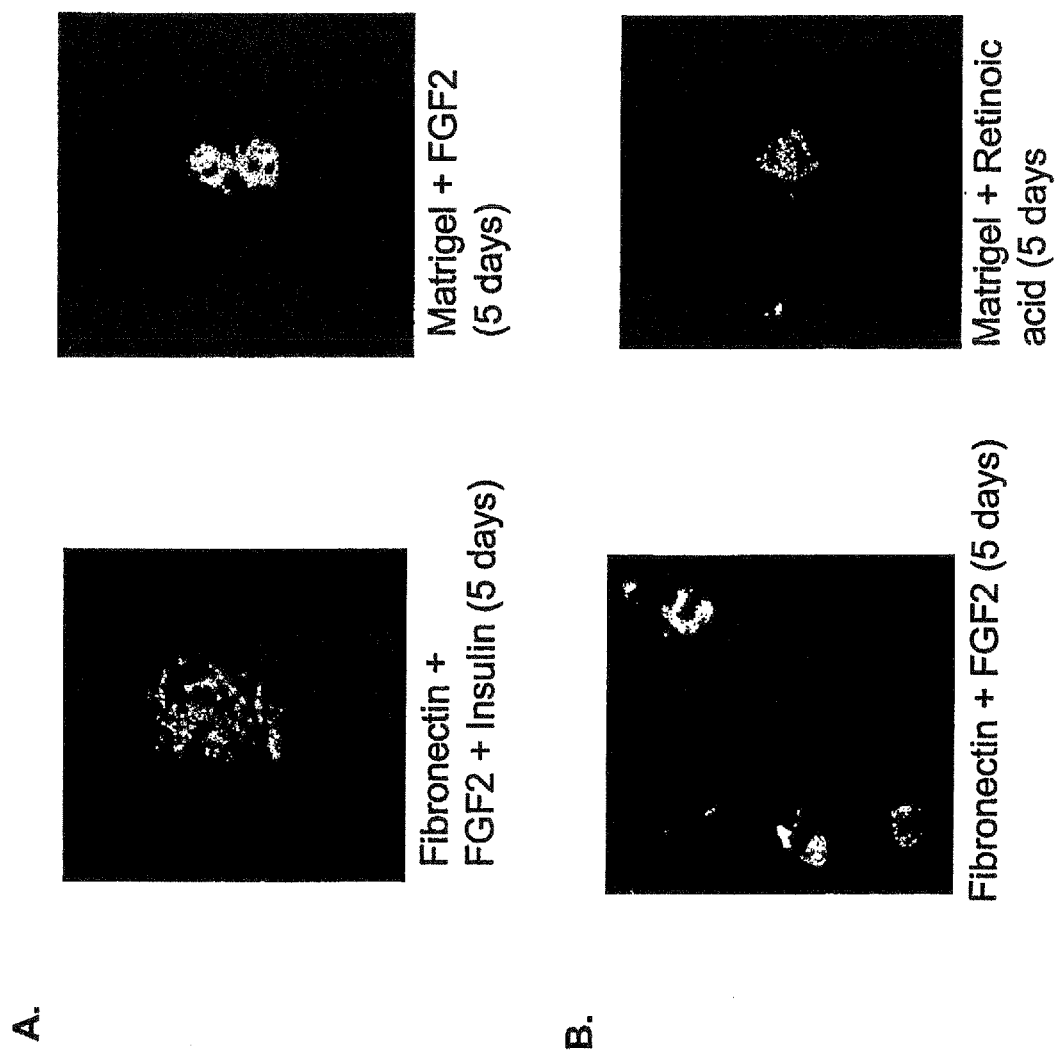
FIG. 3 is a photographic representation of Müller cells cultures under various conditions, with (A) showing expression of cyclin D and (B) showing binding to peanut agglutinin.
Figure 4:
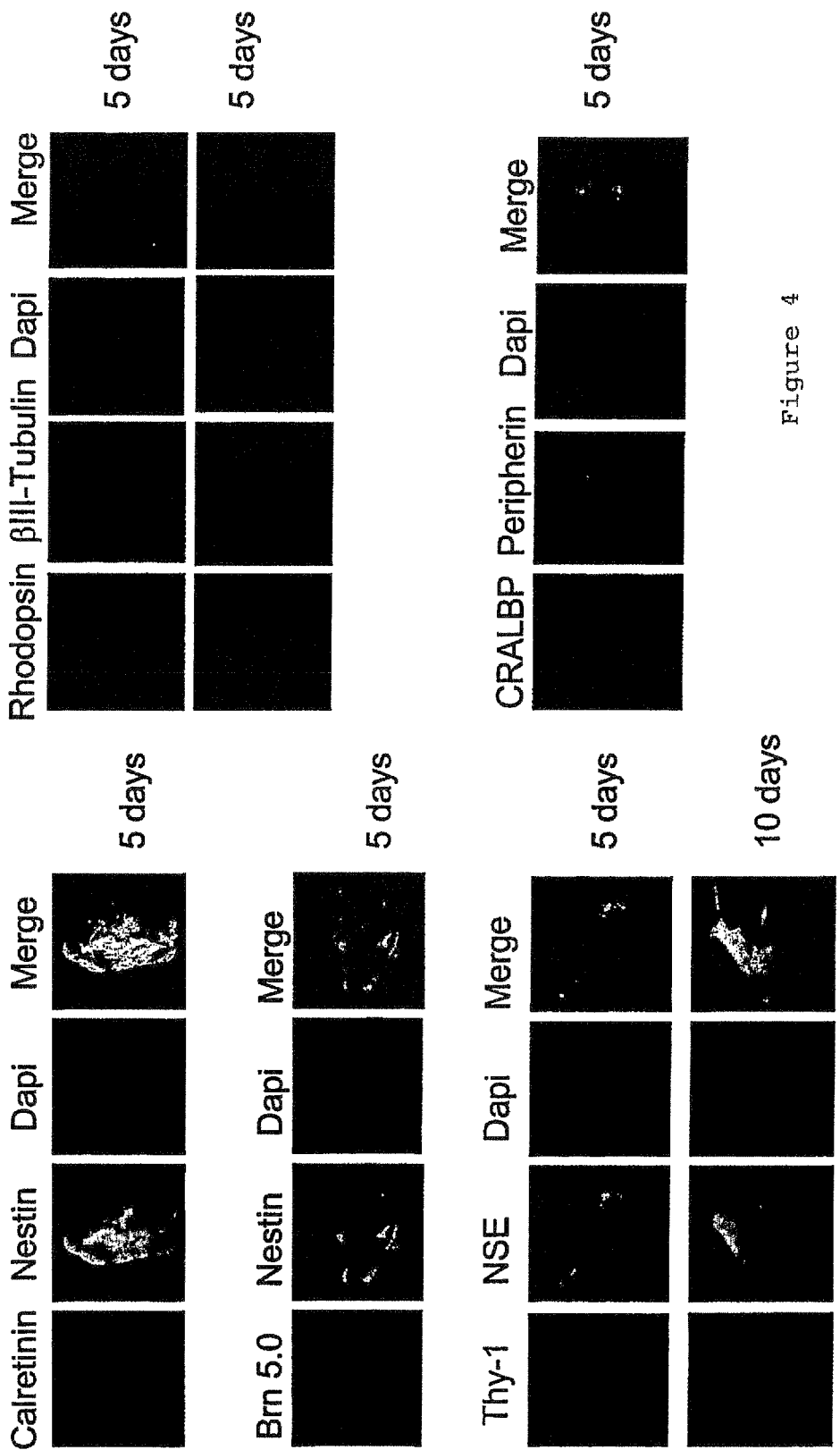
FIG. 4 is a photographic representation of the expression of retinal neural markers by Müller cells cultured on matrigel in the presence of retinoic acid.

In order to produce the de-differentiated Müller cells, it is necessary to culture the isolated adult Müller cells in the presence of an extracellular matrix protein and a growth factor. Extracellular matrix proteins are complex proteins that surround and support cells with an organ. Suitable extracellular matrix proteins will be known to the skilled person, and include matrigel, fibronectin, collagen, vitronectin and laminin. The culture conditions also require a growth factor to aid de-differentiation. Suitable growth factors will be apparent to the skilled person and include epidermal growth factor (EGF), fibroblast growth factor-2 (EGF-2), insulin-like growth factor-1 (IGF-1). The preferred growth factor is epidermal growth factor (EGF). The morphology of Müller cells under different culture conditions is shown in FIG. 2.

Culturing the adult Müller cells in these conditions allows de-differentiation to occur, leading to Müller cells that express nestin, βIII tubulin and bind peanut agglutinin, which are known markers of embryonic neural cell progenitors. These markers can be identified readily using conventional antibody-based detection systems, e.g. immuno-cytochemistry and immuno-blotting (Limb et al., Invest. Ophthalmol. Vis. Sci., 2002; 43: 864-869 and Lewis et al., Am. J. Ophthalmol., 1994; 118: 368-376).

The de-differentiated cells may be used in this form or may be differentiated into a particular cell phenotype, using specific differentiation agents. For example, in the presence of retinoic acid (RA), a well known differentiating agent of stem cells, the Müller cells form a mosaic of cells resembling ganglion cells and express a low molecular weight neuro filament protein and neuron-specific enolase, characteristic markers of neural cells. Other suitable differentiation agents include 3,3',5-Triiodo-L-thyronine, insulin, and TGFβ. Combinations of differentiating agents may be used to form particular phenotypes. For example, the combination of FGF2 and IGF-1 induce human Müller progenitor cells to express Thy-1, neuron-specific enolase (NSE) (markers of major retinal neurons such as ganglion cells) and Peripherin (expressed by cones and rod photoreceptor cells). In this way, a specific phenotype can be produced for the treatment of a condition associated with the loss of, or damage to, that particular type of cell. The method of the invention therefore allows large numbers of specific cell types to be prepared and used in therapy.

In addition, the method of the invention permits multiple layers of retinal cells to be prepared, each layer having a different phenotype. The Müller cells can be made to differentiate into different specific retinal neurons and placed on matrix substances which are layered to produce a retinal structure for grafting.

The differentiation of the Müller cells may also be influenced by the local environment on administration to a patient. In damaged areas, growth factors are produced which may determine the ultimate phenotype of the transplanted Müller cells. The de-differentiated Müller cells may therefore be administered to a patient and adopt the phenotype of the damaged cells, replacing the lost or damaged cells.

The establishment of initial Müller cell lines in the defined culture conditions may be time dependent and it is preferable to culture the isolated Müller cells for at least 2-3 weeks following the addition of the growth factor.

Colonies of cells are formed in the culture media and these may be isolated and placed in new culture media to generate a large number of cells.

The cultured and de-differentiated Müller cells are said to be immortal in that they may be maintained and expanded in culture for multiple passages and retain the ability to differentiate into different phenotypes in response to differentiating agents.

The cells may be used in the treatment of a condition associated with cell loss or cell damage in a mammalian eye. Conditions that may be treated by transplanting the cells of the invention include age-related macular degeneration, macular hole non-proliferative diabetic retinopathy, proliferative diabetic retinopathy, proliferative vitreoretinopathy, retinal detachment, retinitis pigmentosa, glaucoma and optic nerve injury. Other types of inherited and non-inherited retinal degeneration may also be treated.

The cells used in the treatment of humans should preferably be derived from human cells to reduce problems with immune rejection. The cells may be autologous cells (derived from the mammalian eye to be treated), heterologous cells stored in a cell bank, or genetically modified cell lines derived from these cells.

To treat a patient it is generally of assistance to know where damage has occurred in the eye. Once the existence of damage has been established, whether it be in one isolated area or in several areas, treatment by implantation of cells into the damaged area may be carried out. The cells may be transplanted at a single site, or preferably at multiple sites.

After treatment the progress of the patient may be monitored using tests known to examine cortical visual function. Suitable monitoring techniques include: i) psychophysical tests such as visual field and contrast sensitivity tests, ii) electro-physiological tests such as electro-retinogram (ERG), and iii) high resolution imaging techniques such as ocular coherence tomography (OCT).

Preferably, treatment will substantially correct a visual impairment. However, treatment according to the present invention and with the cells, medicaments and pharmaceutical preparations of the invention, may lead to improvement in function without complete correction. Such improvement will be worthwhile and of value.

The number of cells to be used will vary depending on the nature and extent of damage. Typically, the number of cells used in transplantation will be in the range of about 100,000 to several million. Treatment need not be restricted to a single transplant. Additional transplants may be carried out to further improve function. The cells prepared according to the invention may be formulated with any pharmaceutically acceptable diluent or excipient and may include additional pharmaceutical agents, including immunosuppressive agents or growth factors. The cells may also be genetically modified to express other pharmaceutical agents which may be required at the site of damage.

The cells may also be combined with agents known to plasticize the nervous system, which may enhance the ability of the cells to connect to the nervous system and to grow into the eye.

The following Examples illustrate the invention.

EXAMPLE 1

De-Differentiation of Adult Müller Progenitor Cells into Cells Expressing Markers of Retinal Neurons Müller cells in suspension were cultured on matrigel coated culture plates at a density of 1000 cells/ml in DMEM medium containing 10% foetal bovine serum (FCS) and either FGF-2 (40 µg/ml) alone or in combination with insulin (100 µg/ml), ii) retinoic acid (RA) (500 nM), or iii) triiodothyronine (T3, 40 µg/ml). Following 3-10 days in culture with medium freshly replaced every 48 hours, cells exhibited various changes in morphology and expression of neural retinal markers. For example, following 5 days in culture on Matrigel and in the presence of FGF2, cells formed neurospheres and cells contained in the neurospheres bound PNA and expressed nestin, calretinin and βIII tubulin (markers of neural progenitors). When cultured on fibronectin in the presence of retinoic acid, Müller cells formed neurospheres and also displayed neural morphology. They also expressed nestin and markers of retinal neurons including 68 kD neurofilament protein, thy-1 and calretinin, as well as rhodopsin, a marker of rod photoreceptor cells. Following 10 days in culture on matrigel in the presence of FGF2 and IGF-1, they displayed neural morphology and expressed the retinal neural markers thy-1, neuron-specific enolase and calbinding. In addition, they expressed rhodopsin and peripherin, both markers of photoreceptor cells.

EXAMPLE 2

Restoration of Visual Function in an Experimental Models of Retinal Degeneration Three week-old dystrophic Royal College of Surgeons (RCS) rats, which exhibit progressive photoreceptor degeneration accompanied by ganglion cell loss, were immunosuppressed with cyclosporine A and injected via a transscleral route into the dorso-temporal subretinal space with 2 µl of DMEM medium containing $10^5$ Müller cells. Retinal architecture and localization of the transplanted cells were examined at 8, 12 and 15 weeks after transplantation using histo-pathological and immuno-histochemical techniques. Visual function was measured by timing the animals' head movement in a set interval, when placed on a stationary platform in the centre of a rotating drum lined with black and white stripes. Using this experimental protocol, if the rat can see, the moving lines evoke an involuntary optokinetic response such as the rat track the movement. The results showed that human Müller stem cells transplanted into the subretinal space of RCS rats migrated across the retina and localized into the photoreceptor and ganglion cell layers.

Figure 6:
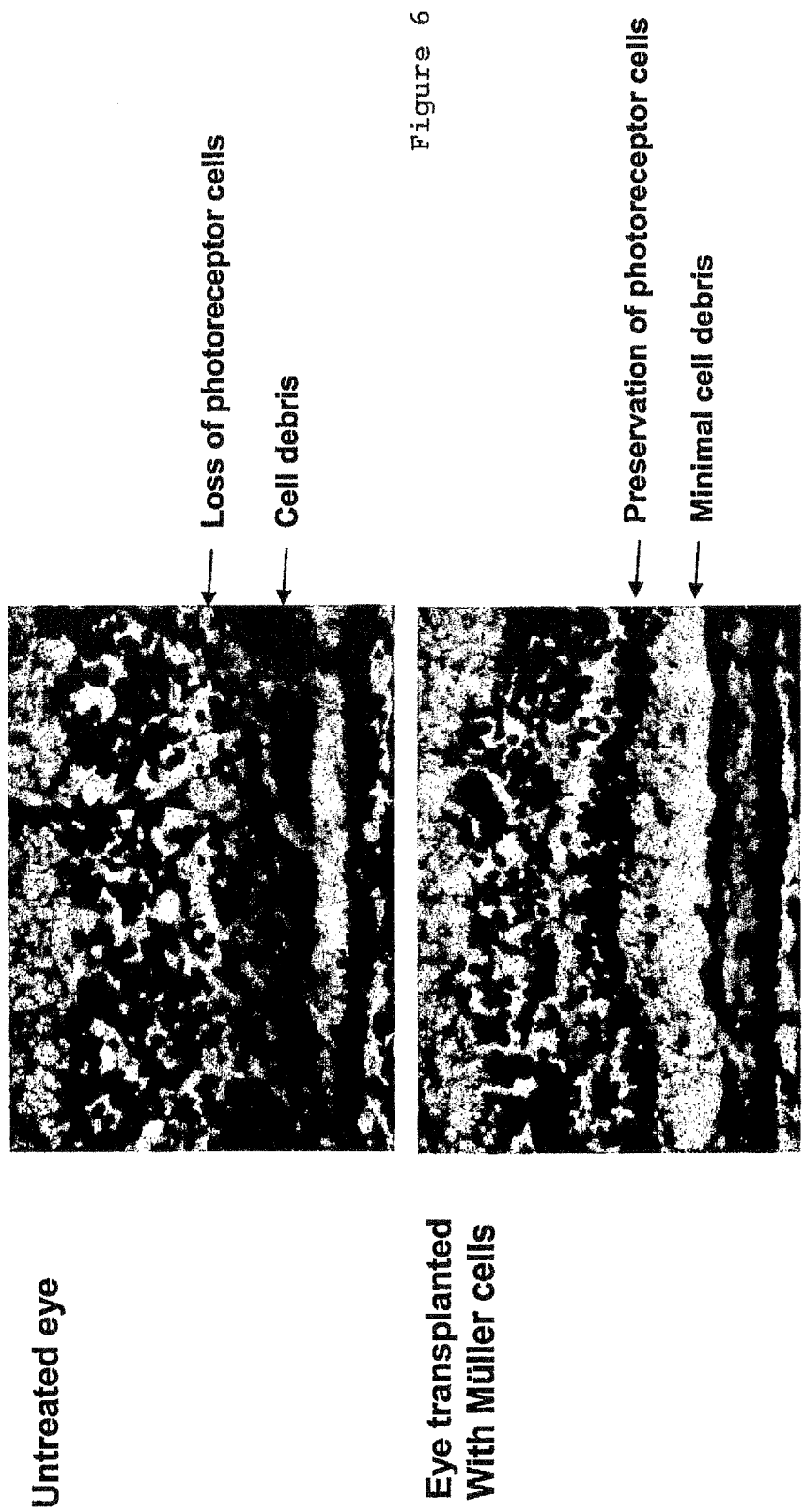
FIG. 6 is a photographic representation of Müller cells transplanted into RCS rats, and shows the retinal appearance after 4 months post-transplantation.

Examination of retinal morphology in the transplanted rats showed that the photoreceptor cell layer and general retinal appearance were well preserved (see FIG. 6). They also showed that transplanted Müller stem cells preserved visual function in the RCS rat, as judged by head tracking responses.

EXAMPLE 3

Pluripotentiality of Müller Stem Cells In vitro

Resembling that observed with neural progenitors of the rat, mouse and chick retinae, a large proportion of cells present in the de-differentiated cells expressed i) cyclin D, a cell cycle protein involved in the regulation of proliferation during retinal development; ii) binding of peanut agglutinin, a lectin that binds to glycoconjugates of pluripotent neural stem cells; iii) calretinin, a major neural retinal marker; iv) nestin and βIII tubulin, early markers of neural differentiation; and v) markers of neural retinal progenitors, including Six 3/6 and Sox-2. These cells appeared to give origin to different mature retinal neurons, as shown by the heterogeneity of neural retinal markers they expressed. These included Thy-1, NSE, Brn 5.0, HuD, peripherin, calretinin and rhodopsin.

After 5-7 days, cells exhibited morphological features and markers of differentiated retinal neurons. However, according to the extracellular matrix and growth factors used for de-differentiation, there was variability in the proportion of cells expressing different markers as well as in the pattern of expression of these molecules. This is illustrated by observations that Pax-6 staining was mainly cytoplasmic in cells cultured on BMP alone or on FN with FGF-2, but that nuclear staining for this factor predominated in cells cultured on BMP with FGF-2 or RA. Cytoplasmic staining for Six 3/6 was observed in cells cultured on FN or BMP in the presence of FGF-2, whilst nuclear staining for this factor was seen in cells cultured on basement matrix protein (BMP) with retinoic acid (RA). Staining for Sox-2 was characteristically associated to cytoplasmic and neurite extensions and cells cultured on FN or BMP with FGF-2 displayed characteristic bipolar morphology and expression of peripherin, resembling photoreceptor cells. Neurite extensions of up to 250 µm long were observed when cells were stained for this molecule. Expression of PKC and Chx10 was predominantly cytoplasmic, whilst Sonic hedgehog protein (Shh) expression was characteristically dense around the nuclei. However, nuclear association of this factor predominated in cells cultured on BMP with RA.

In addition to these differences, exposure to various culture conditions resulted in variability in the proportion of cells expressing individual markers. When cultured on BMP with RA, 17-19% of cells expressed Pax-6, compared with 82% of cells cultured on fibronectin in the presence of FGF-2. A large proportion of cells (71%) maintained the expression of CRALBP when plated on FN with FGF-2, in contrast to <18% cultured in the presence of BMP and RA or FGF-2. Sox-2 was expressed by 50-88% of de-differentiated Müller stem cells independent of the substrate and growth factor used, whilst a large proportion (85%) of cells expressed HuD when cultured on FN in the presence of FGF-2.

A relatively large number of cells expressing peripherin (22-29%), Shh (39-40%), Chx10 (15-21%) and PKC (29-33%) was also observed when cells were cultured in the presence of FGF-2.

EXAMPLE 4

In situ Expression of Progenitor Markers by Müller Cells of the Adult Human Retina Evidence that pluripotent stem cells isolated from adult neural retina constitute a population of Müller cells could only be confirmed if these cells were to be identified in situ. Therefore, retinal sections were co-stained with antibodies to various markers of retinal progenitors and the Müller cell markers CRALBP or nestin. Confocal microscopy showed that a population of cells localized in the neural central retina, with characteristic Müller cell morphology and expressing CRALBP, expressed the progenitor markers Shh, Sox-2 and Chx10. Although the frequency of Müller cells co-expressing these markers is higher in the peripheral (2-5% of the total number of cells in the inner nuclear layer (INL)) than in the central retina (1-2% of cells in the INL), cells were clearly observed at a distance of 2.0-2.5 cm from the ciliary body. Co-staining of retinal sections for nestin also identified Müller cells co-expressing this progenitor marker and the transcription factors Shh, Sox-2 and Chx10. Co-staining of Müller cells for progenitor markers was observed in all four specimens examined. These observations strongly support the observations that a population of Müller cells from the adult human neural retina has pluripotent characteristics and that they can be easily isolated and maintained indefinitely in vitro.

EXAMPLE 5

Figure 7:
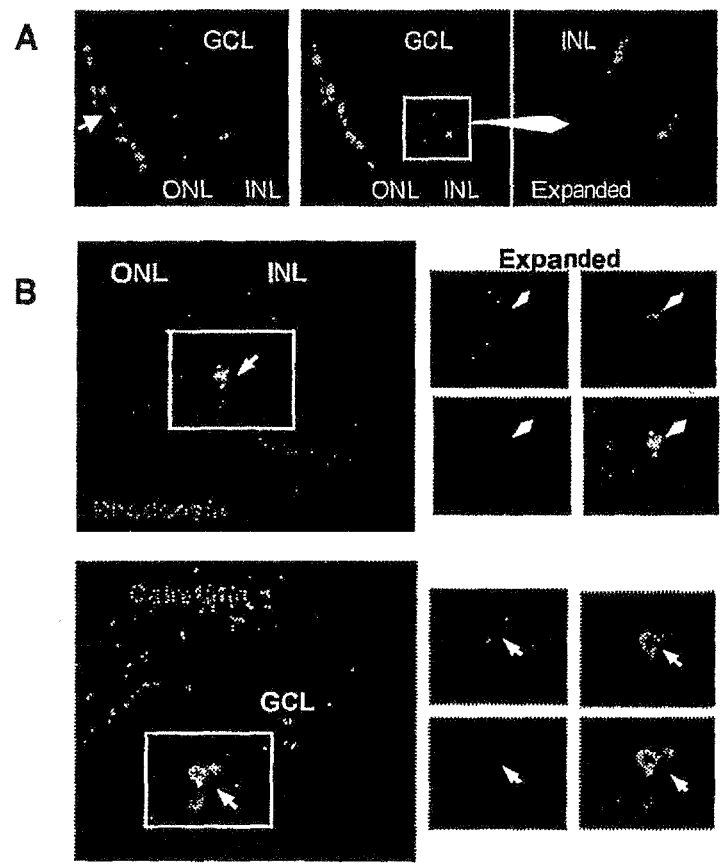
FIG. 7 is a photographic representation of Müller cells transplanted into the subretinal space of a RCS rat, with the cells identified by antibody markers.

Fate of Müller Progenitor Cells Upon Grafting into the Subretinal Space of the RCS Rat By tracing grafted Müller stem cells with antibodies to human mitochondria, it was observed that, 7-9 days after subretinal injection, cells were grouped in small clusters along the surface of the outer nuclear layer (ONL) and that some cells had migrated into the retinal cell layers (FIG. 7A). Cells that had migrated into the photoreceptor cell layer expressed rhodopsin, a rod specific marker (FIG. 7B), whilst cells that had migrated into the ganglion cell layer (GCL) expressed calretinin (FIG. 7B), a marker of ganglion cells. Similar pattern of migration and localization of the transplanted cells was observed at 5 weeks after transplantation.

EXAMPLE 6

Grafting of Müller Stem Cells Preserves Retinal Integrity and Visual Function in Dystrophic RCS Rats Analysis of retinal morphology following 15 weeks after Müller stem cell graft showed a good preservation of retinal integrity, as judged by the anatomical organization of photoreceptor cells in the ONL and normal morphology of the outer segments. Full thickness of the ONL was seen in one of the animals and contrasted with the sparse presence of photoreceptor cells in the non-transplanted contra lateral retina (FIG. 6).

Figure 8:
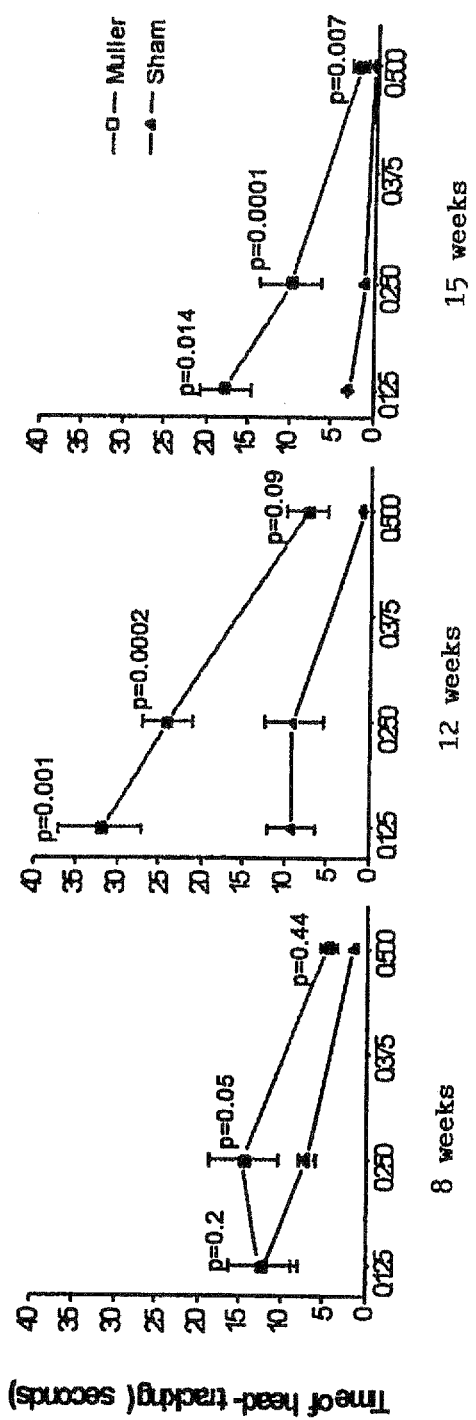
FIG. 8 is a graphic representation of the response to visual stimuli of a RCS rat after transplantation with the Müller cells of the invention.

Visual function, as determined by head-tracking experiments showed that rats transplanted with Müller stem cells were able to track all grating stimuli significantly better than sham operated animals. This ability to respond to visual stimuli was much greater at 12 and 15 weeks than at 8 weeks after transplantation (FIG. 8). At 8 weeks transplanted animals did not show a difference from sham operated rats when tracking a visual stimulus of 0.125 cycles per degree, but at gratings of 0.25 and 0.5 cycles per degree, transplanted animals tracked significantly better than sham operated rats. After 15 weeks, a decreased visual response to all grating stimuli was observed in the transplanted animals, although this response was significantly higher than in the sham operated rats.

We claim:

1. A method for introducing photoreceptor cells into an eye photoreceptor layer, comprising:
   a. inducing mammalian adult Muller cells to de-differentiate into retinal cells expressing nestin, calretinin and βIII-tubulin;
   b. inducing the retinal cells to differentiate into cells expressing photoreceptor markers rhodopsin and peripherin; and
   c. directly transplanting to the damaged area of a mammal's eye in vivo an effective amount of the cells expressing said photoreceptor markers,
   wherein the transplanted cells migrate into the photoreceptor cell layer of the mammal's eye, or the transplanted cells express rhodopsin after said transplanting, or both.

2. A method for introducing retinal ganglion cells into an eye ganglion cell layer, comprising:
   a. inducing mammalian adult Muller cells to de-differentiate into retinal cells expressing nestin, calretinin and βIII-tubulin;
   b. inducing the retinal cells to differentiate into cells expressing retinal ganglion cell markers Thy-1 and NSE; and
   c. directly transplanting to the damaged area of a mammal's eye in vivo an effective amount of the cells expressing said retinal ganglion cell markers,
   wherein the transplanted cells migrate into the ganglion cell layer of the mammal's eye, or the transplanted cells express calretinin after said transplantation, or both.

3. A method for treating photoreceptor degeneration, comprising:
   a. inducing mammalian adult Muller cells to de-differentiate into retinal cells expressing nestin, calretinin and βIII-tubulin;

b. inducing the retinal cells to differentiate into cells expressing photoreceptor markers rhodopsin and peripherin;
c. directly transplanting to the damaged area of a mammal's eye an effective amount of the cells expressing said photoreceptor markers; and
d. permitting the transplanted cells to migrate into the photoreceptor cell layer of the mammal's eye, wherein the eye receiving the transplanted cells exhibits involuntary eye tracking movement at a higher response compared to an eye not receiving the transplanted cells.

4. A method for treating retinal ganglion cell degeneration, comprising:
a. inducing mammalian adult Muller cells to de-differentiate into retinal cells expressing nestin, calretinin and βIII-tubulin;
b. inducing the retinal cells to differentiate into cells expressing retinal ganglion cell markers Thy-1 and NSE;
c. directly transplanting to the damaged area of a mammal's eye an effective amount of the cells expressing said retinal ganglion cell markers; and
d. permitting the transplanted cells to migrate into the ganglion cell layer of the mammal's eye, wherein the eye receiving the transplanted cells exhibits involuntary eye tracking movement at a higher response compared to an eye not receiving the transplanted cells.

\* \* \* \* \*

UNITED STATES PATENT AND TRADEMARK OFFICE
CERTIFICATE OF CORRECTION

PATENT NO.       : 8,691,207 B2                     Page 1 of 1
APPLICATION NO.  : 13/341042
DATED            : April 8, 2014
INVENTOR(S)      : Gloria Astrid Limb et al.

It is certified that error appears in the above-identified patent and that said Letters Patent is hereby corrected as shown below:

In the Claims

Column 8
Line 37, "adult Muller cells" should read --adult Müller cells--
Line 51, "adult Muller cells" should read --adult Müller cells--
Line 65, "adult Muller cells" should read --adult Müller cells--

Column 9
Line 14, "adult Muller cells" should read --adult Müller cells--

Signed and Sealed this
Fifteenth Day of July, 2014

Michelle K. Lee
*Deputy Director of the United States Patent and Trademark Office*